(12) United States Patent
von Lerber (10) Patent No.: US 6,512,230 B1
(45) Date of Patent: Jan. 28, 2003

(54) METHOD AND AN ARRANGEMENT FOR INITIATING RADIATION ABSORPTION MEASUREMENTS OF GASEOUS MEDIA

(75) Inventor: Tuomo Antero von Lerber, Espoo (FI)

(73) Assignee: Instrumentarium Corp., Helsinki (JP)

( * ) Notice: Subject to any disclaimer, the term of this patent is extended or adjusted under 35 U.S.C. 154(b) by 0 days.

(21) Appl. No.: 09/571,540

(22) Filed: May 16, 2000

(30) Foreign Application Priority Data

Jun. 18, 1999 (EP) .............................................. 99660111

(51) Int. Cl.⁷ .............................................. G01N 21/35
(52) U.S. Cl. .................................................. 250/339.13
(58) Field of Search ................................... 250/339.13

(56) References Cited

U.S. PATENT DOCUMENTS

| | | |
|---|---|---|
| 4,587,427 A | 5/1986 | Talbot et al. |
| 5,070,245 A | 12/1991 | Rantala et al. |
| 5,092,342 A | 3/1992 | Hattendorff et al. |
| 5,210,702 A * | 5/1993 | Bishop et al. ................ 702/24 |
| 5,693,945 A | 12/1997 | Akiyama et al. |
| 5,793,043 A * | 8/1998 | Weckström et al. ... 250/339.13 |

FOREIGN PATENT DOCUMENTS

| | | |
|---|---|---|
| EP | 510 856 A2 | 10/1992 |
| GB | 2 313 198 A | 11/1997 |

* cited by examiner

Primary Examiner—Constatantine Hannaher
(74) Attorney, Agent, or Firm—Andrus, Sceales, Starke & Sawall, LLP (57) ABSTRACT

The invention relates to an arrangement in an apparatus for analyzing, on the basis of radiation absorption properties, one or more gas component included in a gaseous medium from an origin, like exhaled air from a person. The apparatus comprises a radiation source (10); a measuring chamber (8) provided with radiation transmissive windows (7a, 7b) for receiving a gas mixture (6) from at least the gaseous medium (G1); a first detector (1), which receives the radiation passed through the gas mixture; and between the radiation source and the detector a first optical interference filter (3), which has a first radiation transmission wavelength band and which is tiltable (P) relative to the passing radiation (R) beam. The arrangement further comprises a second detector (2) directed towards a radiation input surface (5b) of the first interference filter, said second detector receiving momentarily a portion of said radiation (R) as reflected from said radiation input surface (5b) of the first interference filter (3) during the tilt (P) movement.

41 Claims, 5 Drawing Sheets

METHOD AND AN ARRANGEMENT FOR INITIATING RADIATION ABSORPTION MEASUREMENTS OF GASEOUS MEDIA

BACKGROUND OF THE INVENTION

The invention relates to an arrangement in an apparatus for analyzing, on the basis of radiation absorption properties, one or more gas component included in a gaseous medium from an origin, said apparatus comprising: a radiation source; a measuring chamber provided with radiation transmissive windows for receiving a gas mixture from at least the respiratory air of a person; a first detector, which receives the radiation passed through the gas mixture in said chamber; and between the radiation source and the detector a first optical interference filter, which has a first radiation transmission wavelength band and which is tiltable relative to the passing radiation beam and providing a wavelength shifting of the first radiation transmission band before reaching said first detector directed towards a radiation output surface of said first interference filter. The invention also relates to methods at a process for determining one or more gas component included in a gaseous medium from an origin, whereupon an arrangement defined is used. A specific application of the inventive arrangement and method is to analyze the respiratory air of a person and e.g. the alcohol content of the respiratory air.

Specifically the invention relates to Evidential Breath Analyzer (EBA) with a device, which measures alveolar ethanol concentration at exhaled air from a person. EBA's are used normally for forensic purposes e.g. detection of intoxicated drivers. The idea to use breath instead of blood has been well known for decades but only recently has international standardization work done in this field. International Organization of Legal Metrology (OIML) has defined error limits for EBA measurements in its recommendation OIML R 126 "Evidential breath analyzers", Edition 1998. The recommendation states the of level physical or physiological disturbances, which are allowed, and not allowed respectively, to affect the final result. One of such influencing factor is ambient air (e.g. the atmosphere of a room or a car) surrounding the person whose exhaled air is to be measured. Ethanol or other alcohols as well as some other substances in gaseous state can contaminate the ambient air and cause erroneous result.

One widely used technology for EBA's is infrared (=IR) spectrometry. Most IR spectrometers use well-known Lambert-Beer formula $[C=k \cdot \ln(I_0/I)]$ to detect the concentration C of a known substance. In the formula k is a constant, the value of which depends on the device, the substance to be analyzed and the units. The ratio of the intensities $I_0$ and $I$ can be determined by various methods. One possibility is to construct and use a reference channel, which is always without any interfering substance, and another possibility is to arrange multiple IR detectors each of them with an IR filter having a transmission band different from those of the other IR filters in front of other IR detectors.

Modern apparatuses, utilizing radiation absorption properties on the basis of non-dispersive methods, for determining one or several gas components, are built without reference gas chamber or reference detectors mainly due the cost reasons. In such device determination of concentration is done in two phases. At the first phase the intensity of radiation is measured when a measurement chamber is filled with non-absorbing reference gas. This intensity is noted as $I_0$ indicating the lack of absorbing substances. This measurement is followed by second measurement where radiation goes through the gas mixture to be inspected/analyzed. This intensity is noted as I. Concentration of inspected substance is calculated using the Lambert-Beer formula disclosed above. The possible weakness of this method is its dependency of reference gas purity-non-purity. If an ambient air is used as reference gas the presence of such substances which are absorbing in the wavelength band used will distort the concentration result. Room or especially car atmosphere may contain and sometimes contain harmful absorbing substances such as isopropanol or octane and the like.

It is known to eliminate the effect of said type of substances on the concentration measurement results of ethanol in case these harmful substances are present in the exhaled air of a person. Publication U.S. Pat. No. 4,587,427 discloses an apparatus and a method utilizing a rotating filter wheel with several side by side arranged filters having narrow transmission bands different from each other, which filters are brought one by one in the IR radiation beam to cause successive signals. The actual ethanol concentration is then determined from these signals with a specified calculation procedure. Exactly the same results as above, but without moving parts, are also achieved by using beam splitters, which are half mirrors, and separate filters in the beams portions divided by the beam splitters. This kind of an apparatus is disclosed in publication U.S. Pat. No. 5,693,945. The beam splitters does not alter the wavelength distribution of the radiation transmitted through and reflected from the half mirrors. A multitude of filters and possible half mirrors make these two alternatives very bulky, expensive and not applicable to mobile use. In a further publication U.S. Pat. No. 5,793,043 discloses an apparatus and a method utilizing a single optical interference filter with a specified transmission band in the radiation beam. This one filter is inclined to different angles in respect to the IR radiation beam, whereupon the wavelengths of the transmission band received by a single detector are shifted as compared to each other causing accordingly different successive signals from said one detector. The actual ethanol concentration is then determined from these different signals with a calculation procedure. These publications do describe means for eliminating the effects of harmful substances in the step of determining the ethanol=alcohol content in the sample of exhaled air, but do not provide any means to detect these harmful substances in a reference gas sample nor provide any means to eliminate the erroneous measurement results caused by these substances if present in the reference gas. These publication do not mention this reference as problem at all, and so the problem remains unsolved.

In a publication GB-2 313 198 another type of measurement device is disclosed comprising an electrochemical measurement cell for determining the ethanol content of the exhaled air and a separate measurement chamber with an IR detector as a reference measurement device as well as a reservoir for storing a calibration substance. Ethanol is used as said calibration substance. During operation the breath air of a person is first of all analyzed for alcohol content using the electrochemical measurement cell, secondly this electrochemical measurement cell is flushed with ambient air, thirdly this cell is allowed gradually fill with the ethanol from the reservoir until the same concentration value is reached as determined in the breath sample of the person, and further this mixture of the ambient air and the ethanol from the reservoir is analyzed in measurement chamber said using the IR detector thereof. This latter measurement result is utilized as a reference to the primary alcohol measurement result received by the electrochemical measurement. In this method the same problems as described above remain unsolved, because the calibration gas mixture used as a reference has ambient air as a solvent, and hence both the sample of the exhaled air and the sample of calibration gas mixture contain all of those harmful substances of the ambient air if present. Because a reservoir for calibrating substance is required and two separate measurement chambers/cells are also needed, this apparatus would necessarily have a very large size. According to this publication these harmful substances are detected and their effect eliminated neither in analyzing the breath sample nor in analyzing the sample of the calibration gas mixture. This publication neither describe the problem discussed nor disclose any means, by which it could be possible to find out these harmful substances or eliminate their effect, and so the method of this publication is much more inferior and provide much lower reliability than the methods of the two publications described above.

SUMMARY OF THE INVENTION

The object of the invention is to achieve a method and an arrangement—in an apparatus for analyzing, on the basis of radiation absorption properties, concentration of one or more gas component included in a gaseous medium from an origin—with which it could be possible to get a reference gas without a need of storing it or any part of it in a reservoir. A second object of the invention is to achieve a method and an arrangement to detect the presence of substances, which may alter absorption properties of the gaseous medium to be analyzed within the spectral range utilized so as to render the measurement result to be erroneous and non-allowable. A third object of the invention is to achieve a method and an arrangement, which could be effectively used in portable or mobile apparatuses. A fourth object of the invention is to achieve a method and an arrangement, which provide conditions to draw up and produce a measuring device of aforesaid type, which has a high reliability and accuracy in spite of the possible presence of the above mentioned absorption altering substances in the ambient air of that origin, a gaseous medium from which is to be analyzed. A fifth object of the invention is to achieve a method and an arrangement, which could be put in practice using as few critical. optical components as possible. A further object of the invention is to achieve a method and an arrangement, which are applicable to devices for analysis of the breath of a person or an animal whether inhaled or exhaled, and which are also proper for evidential breath analyzers.

The above-described problems can be solved and the above-defined objects can be achieved by means of an arrangement of the invention which is characterized by what is set forth in the claims and by means of a method of the invention which is characterized by what is set forth in the claims.

According to the invention the problem described is surprisingly solved by measuring the radiation reflected from an interference filter in a device provided with this kind of a filter, which has a transmission wavelength band and is inclinable to different angles in respect to radiation beam, for identifying the type of and/or determining the concentration of at least one gas component of a gas mixture on the basis of radiation passed through said gas mixture and through said interference filter. According to the further features of the invention all essential harmful substances present in the air ambient to or surrounding the object or origin, from which the gas mixture to be analyzed originates, can be detected surprisingly by using just that ambient/surrounding air as a reference gas. According to still further features of the invention the same detector, which is used for measuring said reflected radiation, is surprisingly also applicable to detect an inclined position of said interference filter and hence utilized to calibrate the interdependency between the inclination angle and the wavelength band shift of said interference filter. Because the minimum amount of optical components and the versatile use thereof and because no special reference gas or an storage thereof is needed, the inventive arrangement and method can be used to have a very compact apparatus. Further advantages of the invention are reach with its other features.

BRIEF DESCRIPTION OF SEVERAL VIEWS OF THE DRAWING

The invention will now be described in detail with reference made to the accompanying drawings.

DETAILED DESCRIPTION OF THE INVENTION

Figure 1:
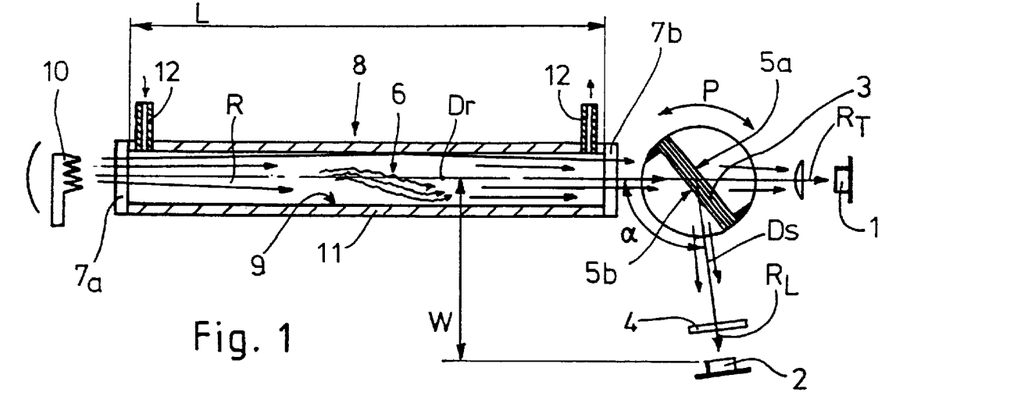
FIG. 1 illustrates schematically in a radiation-oriented section a first embodiment, with an optional second filter, of an arrangement according to the invention for an apparatus suitable for the accurate measurement of gas components.
Figure 2:
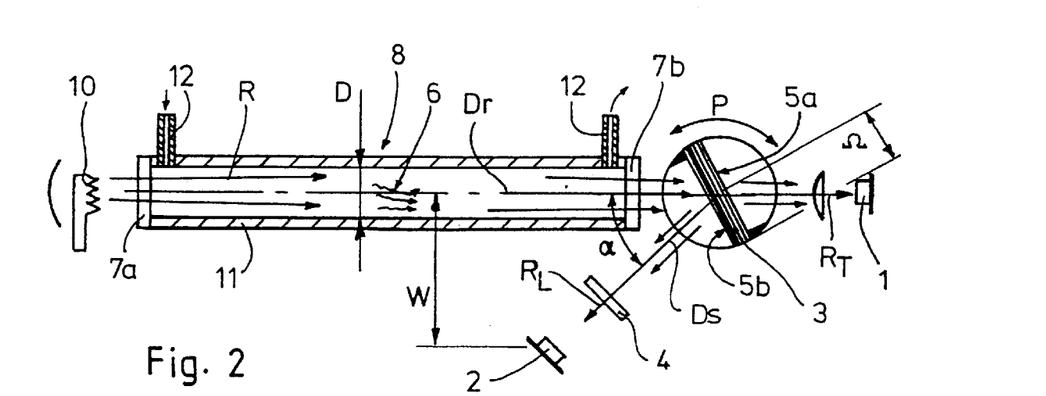
FIG. 2 illustrates schematically in a radiation-oriented section a second embodiment of an arrangement according to the invention for an apparatus suitable for the accurate measurement of gas components.
Figure 3:
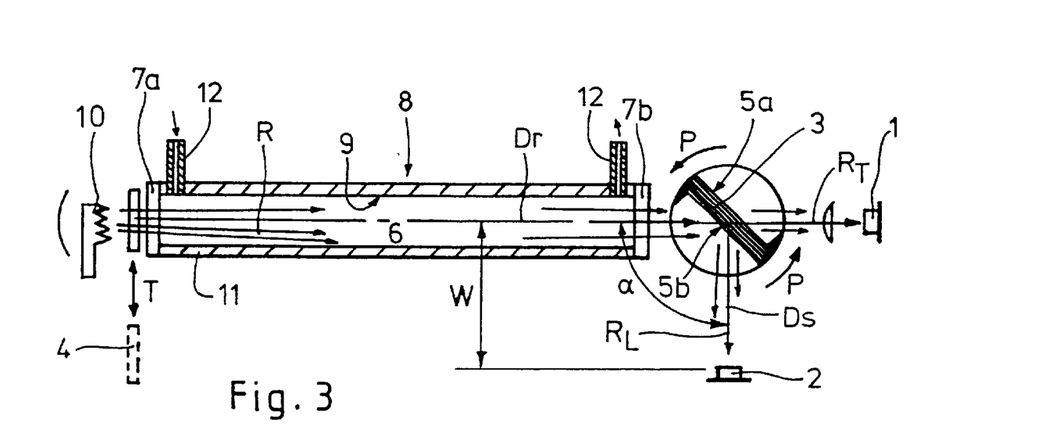
FIG. 3 illustrates schematically in a radiation-oriented section a third embodiment of an arrangement according to the invention for an apparatus suitable for the accurate measurement of gas components.

In FIGS. 1 to 3 are show basic devices according to invention, all of which devices comprise a radiation source 10 emitting infrared radiation R, which have a radiation spectrum providing a wavelength range, within which the transmission band of the tiltable first interference filter 3 in all of its shifted states and the transmission band of an optional second interference filter 4 are included. E.g. a hot filament radiation source is appropriate as an IR emitter. For receiving a sample of a gas mixture the device comprises a measuring chamber 8 provided with radiation transmissive windows 7a, 7b, which normally are opposite each other at the ends of the measuring chamber. In this case the radiation R enters the chamber through the first window and exits the chamber through the second window, whereafter the radiation passes through the tilting first interference filter 3 and reaches finally the first detector 1. The radiation passes once through the gas sample in the measuring chamber 8, whereupon the length L of the chamber is the absorption length of the radiation concerning the sample gas. Alternatively a measuring chamber can be designed having only one trans missive window and a mirror opposite the window, the measuring chamber being therebetween. This alternative embodiment is not shown in the figures. In this latter case the radiation R enters the chamber through the window, reflects from the mirror and exits the chamber through the window, whereafter the radiation passes through the tilting first interference filter 3 and reaches finally to the first detector 1. The radiation passes twice through the gas sample in the measuring chamber 8, whereupon the absorption length of the radiation concerning the sample gas is twice the mechanical length L of the chamber. The first mentioned alternative is more effective, when the ratio of the inner diameter D of the chamber to the inner length L of the chamber is small enough, e.g. 1:5 or smaller, and the chamber wall 11 is non-transparent to radiation as well as the inner wall surface 9 of the measuring chamber have adequate properties, because under these circumstances the radiation R is directed to the first interference filter 3 as a beam, which is within specified angular range. The chamber wall is preferably of a metallic material or the inner wall surface 9 is coated with a metallic material. This is a so called "wave tube" described more detailed in the patent publications U.S. Pat. No. 5,610,400 and U.S. Pat. No. 5,793,043, and excessive optical means, like additional lenses and diaphragms are the avoided by using it. The measuring chamber 8 further comprises an inlet and an outlet 12 for receiving a gas mixture 6.

The device is further provided with a first detector 1, which receives the transmitted radiation $R_T$, i.e. the radiation passed through the gas mixture 6 in the measuring chamber 8. Normally the first detector 1 is in alignment with measuring chamber or "wave tube", and between the radiation source 10 and the first detector 1 is positioned a first optical bandpass interference filter 3, which has a first radiation transmission wavelength band $\lambda 1$, the half-width of which is for instance within a range of 0.3%–4% of the mean transmission wavelength $\lambda c$ thereof, and preferably either between 0.4%–1.5% or between 2%–3% of the mean transmission wavelength. For the purposes of the invention that alternative shown in the figures shall be used, having this first interference filter 3 at exit side of the radiation from the measuring chamber 8, that is between the chamber and the first detector. Placing the first filter 3 e.g. at the input side of the radiation to the measuring chamber is not a proper alternative for the invention. The first detector 1 so receives radiation passed through the gas mixture 6 in the measuring chamber 8 and through the first interference filter 3 exiting the output surface 5a thereof as a transmitted radiation $R_T$ having a radiation intensity $I_T$. This intensity $I_T$ received by the first detector 1 has at least two different values, because of tilting it to various input angles β as described in the next paragraph, which different intensities transformed to signals are utilized for analyzing at least one of the gas components in the gas mixture. The definition "analyze" is used in this application to mean the identification of one or more gas component in a gas mixture and/or measuring the concentration of one or more gas components in a gas mixture. Identification is performed when the chemical compound(s) forming the gas component(s) of interest is/are not known prior to a measurement. Measuring or determining the concentration of known gas components are performed on the basis of the signals from the first detector 1. In many applications, as can be understood on the basis of the examples in this text, the gas component(s) the concentration(s) of which is/are to be measured, are known or determined, and so in these applications at least a concentration of one gas component is measured. For the calculations of concentration(s) and if needed for calculations concerning identification(s) the apparatus is provided with components forming an analyzing calculation unit 24.

Figure 10:
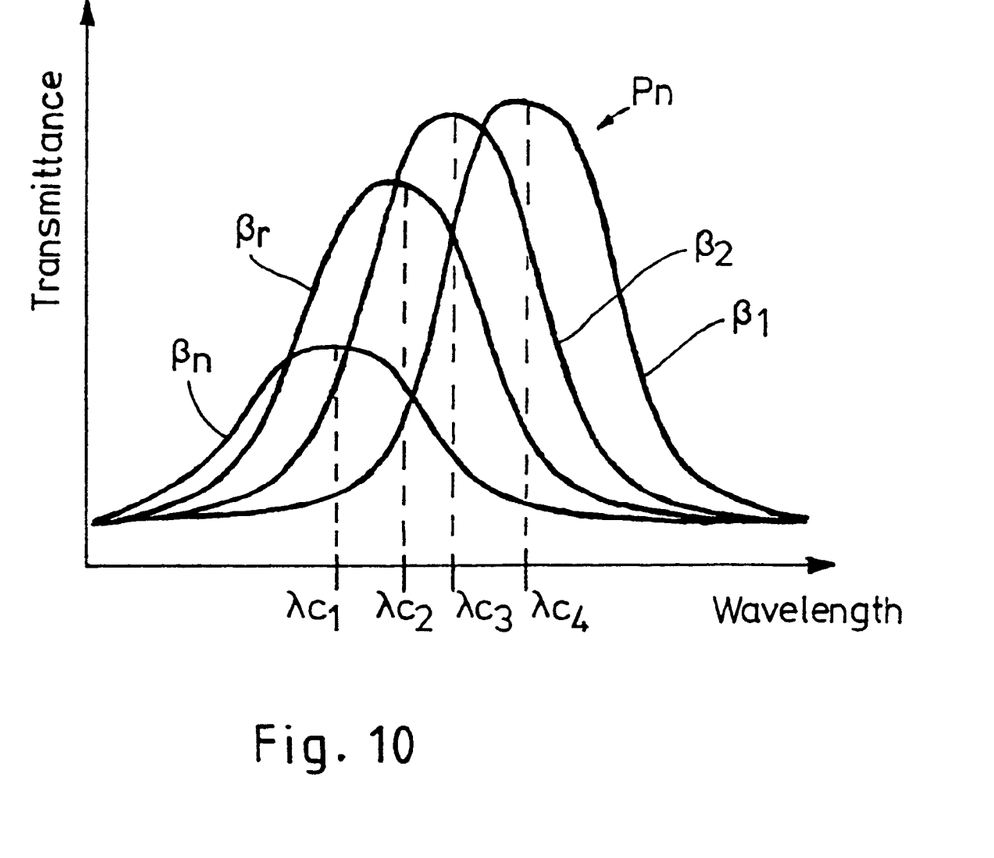
FIG. 10 shows schematically a shifting of the transmission band in general and more specifically the center wavelength of the tilting interference filter.

The first interference filter 3 is tiltable P relative to the passing radiation R beam to a plurality of angularly different inclined positions. This tilting P movement can be arranged either by a pivot mechanism 15 or a rotating mechanism 15—in general a moving unit 15—in a moving unit to turn the filter 3 around an functional axle line 13, whereupon the first interference filter is reciprocated between a maximum input angle β=70° and a minimum input angle β=0°, or rotated over a full circle of 360°, a portion of which is arranged to be input angles β, i.e. angles β from 0° to 70°, which conditions are achieved twice during one total rotation. Typically input angles β between 10° and 60° are utilized. In this text definition "tilt" is used to describe both pivotal and rotational movements to have the angularly different inclined positions Pn of the first filter 3, and said input angle β is an angle between the normal N of input surface 5b of the first filter 3 and the mean direction Dr of said radiation R beam. The tilting movement may be caused around a virtual axle, e.g. placing the first filter in a tubular casing rotatable or pivotable within a cylinder, the casing and the cylinder provided with openings for radiation passage, or a physical axle just around the axle line 13. The axle line 13 is preferably between the outer input surface 5b and the output surface 5a, or in the middle therebetween, as in FIG. 5, whereupon the radiation passes through and reflects from substantially the same area A on the first interference filter 3. It is possible to position the axle line 13 outside the thickness, limited by the input and output surfaces, of the first filter, but no advantages are attained by this construction. As a consequence of this tilting of the first interference filter 3 to several inclined positions Pn is the shifting of the first wavelength transmission band $\lambda 1$, as shown in FIG. 10, where the first transmission band $\lambda 1$ and the shifted mean transmission wavelengths $\lambda c_1$ to $\lambda c_4$ thereof is disclosed in four different input angles β1 to βr to βn. As can readily be understood this one first interference filter 3 functions like several different filters with deviating transmission bands as seen by the first detector 1. Hence the first detector receives different intensities $I_T$ based on different transmission bands and produces accordingly different signals for calculation of concentrations of gas components in that gas mixture fed to the measuring chamber 8.

One of these several inclined positions Pn is a position with an input angle βr for specular reflection of said radiation R to said second detector 2, discussed later in this text.

Said first interference filter 3 is in most cases provided with a limited number of inclined positions Pn for detection, but at least with two inclined positions, which are used for detection of the transmitted radiation $R_T$ passed trough the first filter 3. The number n (=index used in context with the reference numerals and characters) of inclined positions is a predetermined function of the number of the gas components to be taken account from the gaseous medium from a origin, like respiratory air G1 of a person, when determining the concentration of at least one of them. Each of the inclined positions Pn used for detection have a predetermined input angle β1 . . . n for a specific wavelength shift and accordingly a predetermined mean transmission wavelengths λc. Then one alternative to detect the transmitted radiation $R_T$ by the first detector 1 is to stop the tilting movement P of the filter and maintain each of the predetermined inclined positions, with input angles β1 . . . n, for predetermined time periods τ for momentarily guiding of transmitted radiation $R_T$ to said first detector 1. Another alternative is to keep the first filter in continuous tilting movement, either pivot or rotary movement, and to program the first detector 1 to detect at each of the predetermined inclined positions Pn, with input angles β1 . . . n. In this case also the first detector performs each of its detection operations during predetermined time periods τ meaning momentary guiding of transmitted radiation $R_T$ to said first detector 1. Said time periods τ are limited downwards, i.e. to shorter times, by the characteristics of the detectors 1 and 2 and other electronics only, and upwards, i.e. to longer times, by the available overall measuring time required. So this measuring time period τ of each individual measurements at predetermined input angles β1 . . . n can be as long as several second and as short as some microsecond, but nowadays practical values of the time period τ is 300 ms at maximum, or preferably in the range of 50 ms to 150 ms. This same time period τ apply to the detection with the second detector 2 according to the invention, too.

According to the invention the device further comprises a second detector 2, which is directed towards a radiation input surface 5b of the first interference filter 3 and especially so, that the sensitivity direction Ds of this second detector 2 is directed to the area A on the first interference filter 3, which is illuminated by said radiation R exiting from the measuring chamber 8. For this arrangement the inventive second detector 2 is positioned at a transversal distance W off a main radiation R beam directed to said first interference filter 3, and towards the radiated area A on the first interference filter 3. The distance W from the center line main radiation R beam at the measuring chamber 8 is greater than radius Ω of the moving parts in the tiltable first interference filter 3 from its axle line 13. Specifically the sensitivity direction Ds of the second detector 2 is directed to that input surface 5b, opposite to output surface 5a towards which the first detector 1 is directed, of the first interference filter 3, which is illuminated by the radiation R coming from the measuring chamber 8 prior to transmitting/passing through this filter. The second detector 2 and its sensitivity direction Ds is stationary like radiation source 10, measuring chamber 8 and the first detector 1, preferably the first interference filter 3 being the only of the primary optical components, which performs a tilting movement around a stationary axle line 13. When the first interference filter 3 is tilted, as described above, through the input angles β thereof, there is one input angle βr between the main radiation R from the chamber 8 and the normal N to the input surface 5b of the first filter 3, which causes the radiation $R_L$ reflected from the first filter 3 to hit the second detector 2. During this instant the direction of the reflected radiation $R_L$ and the sensitivity direction Ds of the second detector 2 are substantially coincident. Of coarse there is a certain angular sensitivity distribution in the detector 2 and a certain angular distribution in the radiation $R_L$, which means that there is a tolerance range with changing intensity $I_L$ of reflected radiation as seen by the second detector 2 and forwarded as a signal. This is possible because interference filter 3 does not substantially absorb those wavelengths, which are not transmitted through the filter, but reflects them. It behaves as a window for some wavelengths and a mirror for others.

Figure 5:
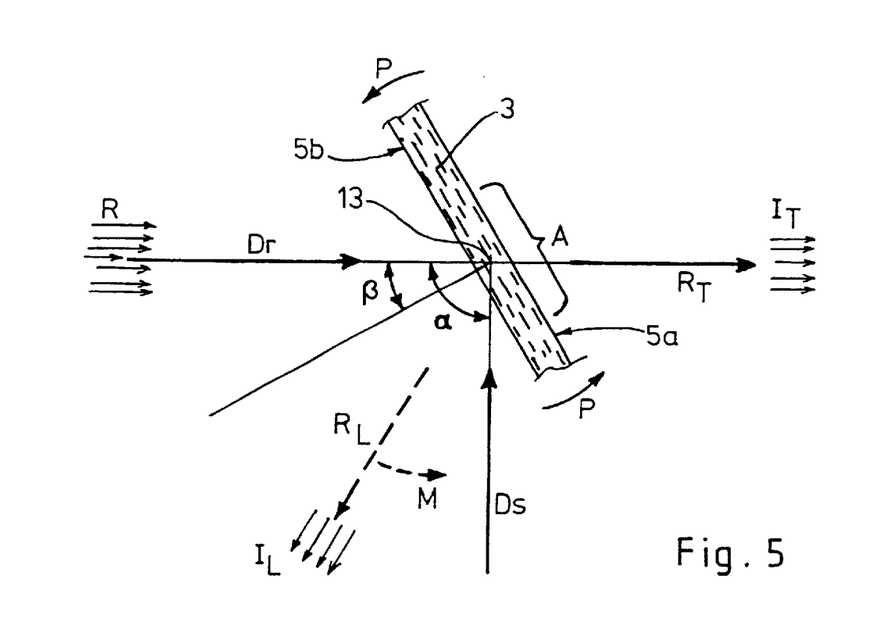
FIG. 5 shows in detail the different directions of the radiation beams at the point of radiation beams crossing and virtual tilting, axle of interference filter according to invention, in the same radiation-oriented section as in FIGS. 1 to 3.
Figure 6:
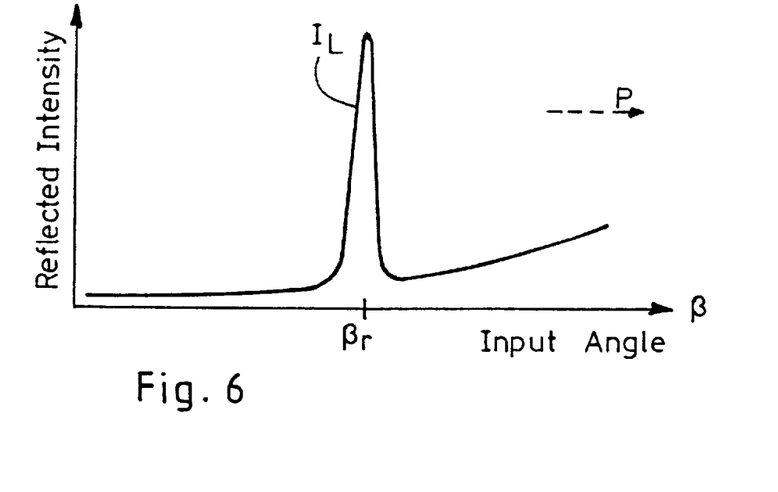
FIG. 6 shows generally the intensity of the radiation reflected from the tilting interference filter as received by the second detector according to invention as function of the tilted angles (=inclination).
Figure 7:
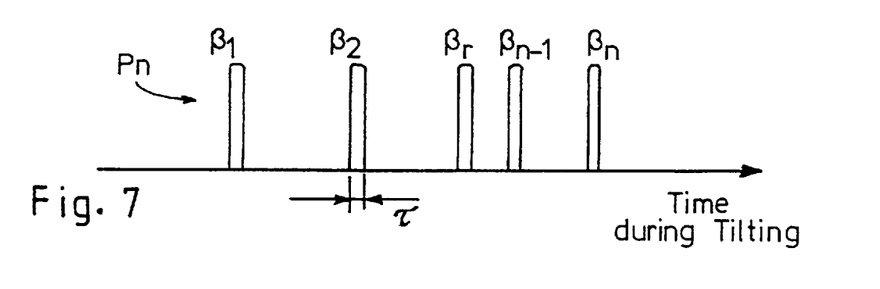
FIG. 7 shows schematically the moments of detection according to invention during the tilting of the interference filter. The momentary detection occasions shown are one of the possible alternatives.
Figure 8:
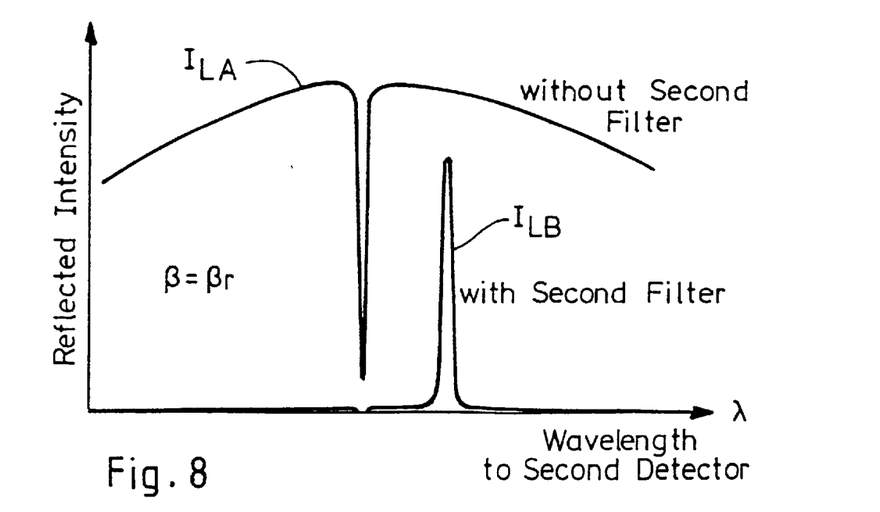
FIG. 8 shows generally the intensity of the radiation reflected from the tilting interference filter as function of wavelengths, that is a wavelength distribution reaching a second detector according to invention. The first curve describes the wavelength distribution without a second interference filter and the second curve describes the wavelength distribution through a second interference filter.

The second detector 2 according to invention is positioned so that an observation angle α from 10° to 140° between a sensitivity direction Ds of said detecting means and the mean direction Dr of the main radiation R beam is established, as shown in FIG. 5. Preferable this said observation angle α of the second detector 2 is designed to be between 30° and 100°, or typically within an angular range of 40° to 70°, to avoid extreme values of input angles β, which lower the efficiency of transmitted radiation $R_T$ as received by the first detector 1. In FIG. 6 it is shown in principle the reflected intensity $I_L$ as seen by the second detector. Over the main part of the tilting movement P, having input angles β, the reflected intensity is very low reaching a maximum at an input angle βr, in which point the main radiation R coming from the measuring chamber is specularly reflected to the second detector 2. At this point the reflected intensity $I_L$ of this specularly reflected radiation $R_L$, as received/seen by the second detector 2, has a slightly variable intensity distribution $I_{LA}$ over a wide wavelength range with an intensity gap $I_G$ at those wavelengths, where the first interference filter 3 has its transmission band λ1, as shown in FIG. 8. At the input angle βr of specular reflection to the second detector the first filter 3 so reflects substantially all other wavelengths but not those passing therethrough to the first detector 1. This has an advantage that the transmitted radiation as filtered by the transmission band λ1 is in correct form continuously available to the first detector 1 for analysis of the gas components of the gas mixture 6, and simultaneously the other parts of the spectrum can be analyzed by the second detector 2. Because the input angle β represents the rate of the tilting movement P, it can be understood and seen e.g. from FIG. 6 that the second detector 2 receives momentarily a portion of the radiation R—wavelength band λ1 subtracted—as reflected from said radiation input surface 5b of the first interference filter 3 during the tilt P movement thereof. It is practical but not necessary to select the input angle βr of specular reflection to be one of the input angles β1 . . . n, which are utilized for determining the gas components of the gas mixture 6. As described earlier in this text, the detection of the reflected radiation $R_L$ can be performed during a continuous tilting—pivot or rotary—movement of the first interference filter 3, including a predetermined time period τ for momentarily guiding of reflected radiation $R_L$ to said second detector 2.

Figure 4:
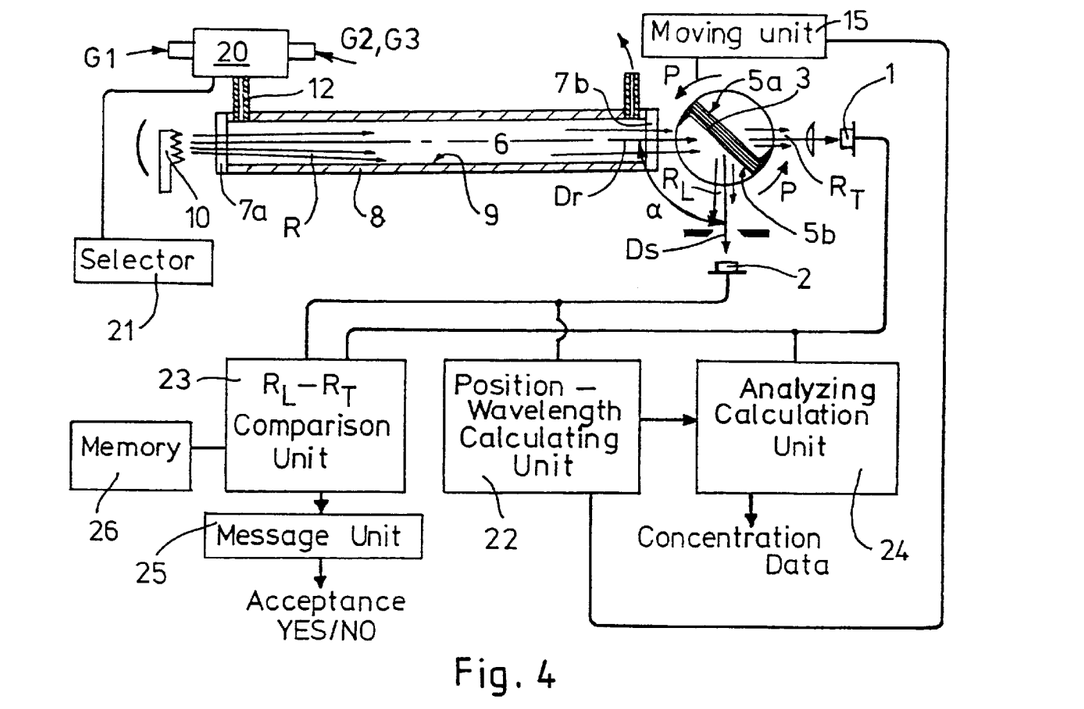
FIG. 4 illustrates schematically, partly in a radiation-oriented section and partly generally, an apparatus of the invention, without a second interference filter, for an arrangement suitable for the accurate measurement of gas components included e.g. in the respiratory air of a person.

In addition the device according to the invention can comprise a second optical bandpass interference filter 4 in the beam of reflected radiation $R_L$, and preferably between the radiation input surface 5b of said first interference filter 3 and the second detector 2. In this described position the second interference filter 4 is kept stationary, that is continuously in the beam of reflected radiation during the tilting movement P of the first interference filter 3, as shown in FIGS. 1 and 4. Alternatively this second filter 4 may be positioned in the beam of the main radiation R, e.g. between the radiation source 10 and the measuring chamber 8, but in this case the second filter 4 shall be driven in the main radiation R for the measuring time period τ of the reflected radiation at the input angle βr of specular reflection, and drawn away for all other measurement time periods τ of the transmitted radiation $R_T$ at the input angles β1 . . . n omitting βr, as shown with dashed line in FIG. 3. The device according to invention as disclosed above do function to detect the presence of those harmful substances, which may be present in the environment of the origin to be tested, and which may alter the concentration measuring result. For a better reliability this aforesaid second interference filter 4 is used, and said second optical bandpass filter 4 has a predetermined second, transmission wavelength band λ2, which deviates from the absorption peaks of those gas components, which are supposed to be present in a reference gas mixture G2. In this case, and at the input angle βr of the specular reflection of the main radiation R to the second detector, the reflected intensity $I_L$ of this specularly reflected radiation $R_L$, as received/seen by the second detector 2, has a narrow intensity distribution $I_{LB}$ at those wavelengths, where the second interference filter 4 has its transmission band λ2, as shown in FIG. 8. At the input angle βr of specular reflection to the second detector, the second filter 3 so creates a narrow intensity band, the intensity of which is based on the transmission band λ2 of the second filter 4 and the transmission properties of the gas mixture 6 in the measuring chamber 8.

Figure 9:
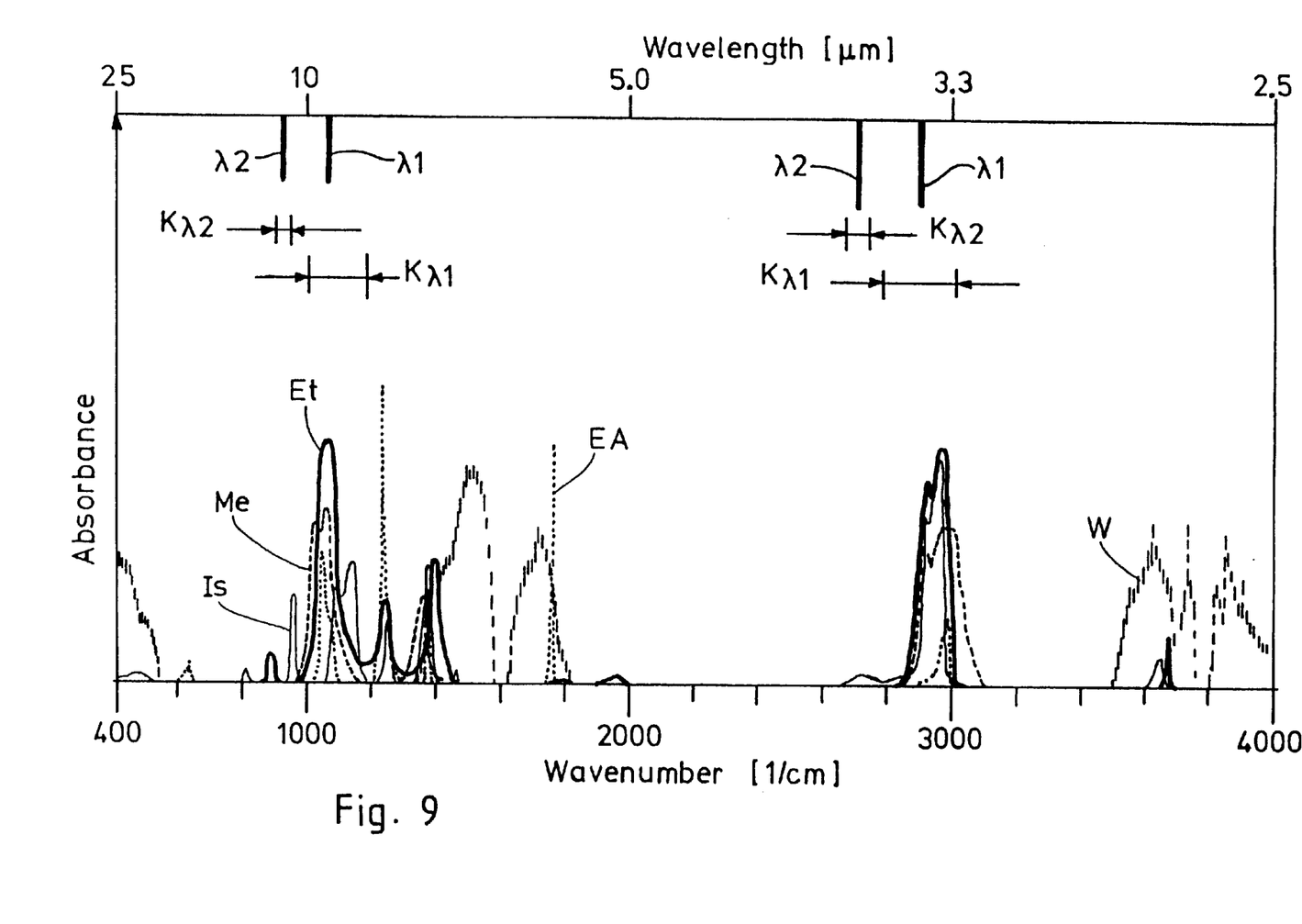
FIG. 9 shows the absorption spectra of some of the gas components relevant in a measurement of a person's respiratory air, and schematically the transmission bands of the tilting interference filter and an optional second interference filter as well the wavelength ranges thereof. The gas components shown are ethanol (Et), methanol (Me), isopropanol (Is), ethyl acetate (EA) and water (W).

The device according to invention is at first calibrated in a well-known environment, e.g. in the factory, where neither harmful gas components, like isopropanol or octane or ethanol from another person, nor those gas components to be analyzed, like ethanol, is present and the signal from both detectors can be measured, as described before. Before this calibration step, it is selected a proper first radiation transmission wavelength band λ1 for the first tiltable interference filter 3, which wavelength band λ1 is included in the wavelength range $K_{\lambda 1}$ of an absorption peak or a group of peaks of that gas component in a gaseous medium G1, like exhaled air from a person, the concentration of which is to be measured. If the second interference filter 4 is used it is also selected a second radiation transmission wavelength band λ2 for this second filter, so that the wavelength band λ2 is included in the wavelength range $K_{\lambda 2}$ of a low absorption, preferably absorption gap, and the second wavelength band λ2 deviates from any of the absorption peaks of those gas components, which are supposed to be present in said reference gas mixture G2. These filters are then of course installed in the device. Preferably should these wavelength ranges $K_{\lambda 1}$ and $K_{\lambda 2}$ be close to each other, side by side or possibly overlapping, as shown in FIG. 9. In case the alcohol content/concentration of the respiratory air of a person shall be measured, the first transmission band λ1 is in the range $K_{\lambda 1}$ of 10 μm±1.5 μm, or in the range $K_{\lambda 1}$ of 3.5 μm±1 μm and have a bandwidth of ±50 nm at maximum. In these cases the second transmission band λ2 is in the range $K_{\lambda 2}$ of 10.6 μm±1 μm, or in the range $K_{\lambda 2}$ of 3.7 μm±0.5 μm.

According to the method of the invention a sample of a calibrating gas mixture G3, which is carefully selected to be pure a gas or a gas mixture of the same type as the gaseous medium G1 to be analyzed later during the normal operation of the device, is fed the measuring chamber 8 as a gas mixture 6. Purity in this context means that the gas mixture G3 contain the normal main components same as the gaseous medium G1 to be analyzed, but not any of those components, whose concentration is to be measured during said actual operation, nor any of the possible harmful substances. In case the operation of the device is intended to measure the ethanol (=alcohol) content of the breath of a person, the gas mixture G3 contains oxygen and nitrogen, but none of ethanol, isopropanol, ethyl acetate, acetone, methanol etc., the absorption spectra of some of these shown in FIG. 9. Next step is passing said radiation R through this sample, and allowing a portion $R_L$ of said radiation R to reflect from the first interference filter 3 and reach the second detector 2, and a portion $R_T$ of said radiation R pass the first interference filter 3 and reach the first detector 1, during the tilting of the first interference filter 3 over said angularly different positions. This aforesaid is a the normal operation of the device. The intensity $I_T$ of the transmitted radiation $R_T$ and an intensity $I_L$ of the reflected radiation $R_L$ are detected by the first and second detector respectively, at the input angle βr of said specular reflection, and a first relationship F1 between a transmitted radiation $R_T$ intensity $I_T$ and a reflected radiation $R_L$ intensity $I_L$ is calculated in the $R_L$–$R_T$ comparison unit 23 of the apparatus and stored in a memory 26.

During use of the apparatus in the field, prior to feeding a sample of the actual gaseous medium G1 to be analyzed into the measuring chamber, a sample of a reference gas mixture G2, which is the available ambient gas mixture surrounding the origin of the gaseous medium G1 and forming a natural part thereof, is fed as a sample into the measuring chamber. In the individual case mentioned above, this reference gas mixture G2 means air around the person, whose breath is to be analyzed, e.g. air within a car or a room or the like, wherever the person is situated. Then the normal operation of the device is started, and the intensity $I_T$ of the transmitted radiation $R_T$ and an intensity $I_L$ of the reflected radiation $R_L$ are detected by the first and second detector respectively, at the input angle βr of said specular reflection, just as described above. Further a second relationship F2 between the transmitted radiation $R_T$ intensity $I_T$ and the reflected radiation $R_L$ intensity $I_L$ is calculated and compared with the first relationship stored in the memory, which is performed in the $R_L$–$R_T$ comparison unit 23 of the apparatus. A signal and/or a change in operation mode of the measuring apparatus is forwarded by the message unit 25 of the apparatus, depending on the difference between the first relationship F1 and the second relationship F2. If the first relationship F1 and the second relationship F2 are same or within specified limits—the difference between relationships F2 and F1 shall be smaller than a specified value, the environmental gas mixture G2, used as a reference, is pure enough (=acceptable) and so the actual concentration measurement of the gaseous medium G1 is allowed. The actual concentration measurement of one or several gas components included in the gaseous medium G1—e.g. alcohol in the exhaled air of a person—is then performed by feeding a sample of this medium G1 as a gas mixture 6 within the chamber 8, and the by measuring the intensities $I_T$ of transmitted radiation $R_T$ at several angularly inclined positions of the first filter 3 and subsequently calculating the concentration data by analyzing calculation unit 24, following a normal procedure partly described above. The calculations are not a subject of this invention and so the details thereof are not described. If the first relationship and the second relationship deviate from each other more than a specified value, the environmental gas mixture G2, used as a reference, is not pure enough (=non-acceptable) and then a further actual measurement is not allowed. The message or signal corresponding acceptance and non-acceptance can be two different audible signals, visual signals or in case of non-acceptance a short time non-operability of the apparatus, provided by message unit 25. These messages as such are details not necessary to be described more in detail.

There are several possibilities to use different types of said relationships, but the most simple and so the preferred relationship is a simple ratio of detected intensities $I_L$ and $I_T$ of the reflected radiation $R_L$ and the transmitted radiation $R_T$, as a formula $F=[I_T/I_L]$. The first ratio/relationship calculated from the calibrating gas mixture G3, $F1=[I_T/I_L]_{calib}$ is stored, and in all subsequent measurements with in each case prevailing reference gas G2, a corresponding ratio/relationship $F2=[I_T/I_L]_{ref}$ between intensities are calculated and compared to ratio/relationship F1 from the calibration. This method is very simple and effective for initiating a process for determining concentrations, especially when the radiation based analysis of gas components are performed according to non-dispersive measuring principles.

According to the method of the invention, at first during each measurement whether in the factory or in the field, the first optical interference filter 1 is tilted over range of angles β thereof, whereupon it is not necessary to detect the transmitted radiation $R_T$ at this stage, and said input angle βr for specular reflection of the main radiation R to a second detector 2 is noticed with the intensity peak $I_L$ at the point of βr, as described earlier in this text and shown in FIG. 6. Next the shifted center wavelength λc of the first radiation transmission wavelength band λ1 of the tiltable first interference filter 3, as seen by the first detector 1, is calculated using a position calculating unit 22 connected to said second detector 2. In this way a connection between each of the predetermined input angles β and the respective shifted center wavelengths $λc_1$, $λc_2$, $λc_3$ etc. and the effective wavelength distributions of the first radiation transmission wavelength band λ1 can be forwarded to analyzing calculation unit 24. This angular position—wavelength—calculation is performed prior to detecting both of the intensities $I_T$ and $I_L$ of the radiation transmitted through and reflected from said first optical interference filter for calculation any ratio/relation-ship F1 or F2.

The apparatus according to invention further comprises a selector 20 and a valve or valves and optionally a pump as a unit 21 for providing said gaseous medium G1 and a reference gas mixture G2 separate from each other as said gas mixture 6 into the measuring chamber 8. These components can be of any known or new type, and are so not described in detail.

The device according to the invention, as described above, can easily be built in a light-weight and portable apparatus. In spite of this the device according to the invention can also be installed e.g. permanently in production apparatuses in a factory or any other large size unit. As described above the most usual way of using the device of invention is to analyze the breath of a person. Generalized this means any process—a human being seen as a process or origin—taking in air through an inlet and removing the air with an altered composition—both through the respiratory tract. In cases of these types the reference gas mixture G2 is the gas mixture supplied to the process/origin in question and the gaseous medium G1 to be analyzed is the gas mixture from a later point of this same process. In special applied cases of the aforesaid general case a special reference gas mixture might be necessary corresponding the properties of the process gasses. It is emphasized, that air is always a useful reference gas mixture G2 independent from the type of gaseous medium G1, that is with any type of gaseous medium. If the absorption peak(s)—and so the transmission band(s) λ1—of the gaseous medium G1 are far from those defined in this text, it might be necessary to select a new second transmission band λ2, which is closer to said first band λ1, for the optional second interference filter 4. When used for process monitoring or testing the device of invention is also capable to detect a leak detection from a pipe or tube carrying a substance or mixture, when the reference gas mixture. It is already described that air from environment to be used as the reference gas mixture G2 is a practical alternative, the gaseous medium being any type. But it is also possible to use, within the scope of the invention, a reservoir containing a reference gas, which is taken from the reservoir for the sample of reference gas and forwarded into the measuring chamber. So it can be seen that the device/arrangement and method according to the invention have many alternative application fields, but breath analysis and especially measuring alcohol concentration from the exhaled air is at least nowadays important.

What is claimed is:

1. An apparatus for analyzing a gas mixture for one or more gas components that may be present in the gas mixture, the analysis of the one or more gas components being carried out on the basis of radiation absorption properties, said apparatus comprising:

a radiation source for providing a radiation beam;

a measuring chamber (6) for receiving a gas mixture, said measuring chamber having at least one radiation transmissive window (7a,7b) for the radiation of said radiation source, radiation from said radiation source passing through the gas mixture in said measuring chamber;

a first detector (1) for receiving radiation that has passed through said measuring chamber;

a first optical interference band pass filter (3) interposed in front of said detector along a path of said radiation beam, said first filter having a surface to which is applied radiation that has passed through said measuring chamber, said first filter having a radiation wavelength transmission band (λ1) for transmitting radiation of the transmission band wavelength through the filter to said first detector, said surface reflecting radiation having wavelengths outside said radiation wavelength transmission band, said first filter being movable to a plurality of positions inclined with respect to the radiation beam for altering said radiation wavelength transmission band of said first filter, movement of said first filter causing movement of the radiation reflected from said surface; and a second detector (2) positioned with respect to said first filter for receiving radiation reflected from said surface when said first filter is moved to a given one of said plurality of positions of said first filter.

2. An apparatus according to claim 1 further including means coupled to said first detector for analyzing a gas component of the gas mixture on the basis of radiation received by said first detector when said first filter is in a plurality of positions.

3. An apparatus according to claim 2 further including comparison means coupled to said first and second detectors for establishing a relationship between the transmitted radiation received by said first detector and the reflected radiation received by said second detector at said given one of said plurality of positions of said first filter.

4. An apparatus according to claim 3 wherein said measuring chamber is further defined as receiving a reference gas mixture, and wherein said comparison means is further defined as establishing said relation for transmitted and reflected radiation when the reference gas mixture is in said measuring chamber for determining a characteristic of the reference gas mixture.

5. An apparatus according to claim 4 wherein said reference gas mixture is ambient air, and wherein said gas mixture is the respiratory air of a person.

6. An apparatus according to claim 1 further including comparison means coupled to said first and second detectors for establishing a relationship between the transmitted radiation received by said first detector and the reflected radiation received by said second detector at said given one of said plurality of positions of said first filter.

7. An apparatus according to claim 6 wherein said measuring chamber is further defined as receiving a reference gas mixture, and wherein said comparison means is further defined as establishing said relationship for transmitted and reflected radiation when the reference gas mixture is in said measuring chamber for determining a characteristic of the reference gas mixture.

8. An apparatus according to claim 7 further comprising selection means for providing the gas mixture to be analyzed or the reference gas mixture to said measuring chamber.

9. An apparatus according to claim 1 wherein said radiation wavelength transmission band of said first filter is in the infrared region of radiation.

10. An apparatus according to claim 9 wherein said radiation wavelength transmission band of said first filter includes a wavelength range of an absorption peak of a gas mixture gas component to be analyzed.

11. An apparatus according to claim 1 further comprising a second optical interference band pass filter interposed in one of said radiation beam and reflected radiation, at least when said first filter is in said given one of said plurality of positions.

12. An apparatus according to claim 11 wherein said second filter is positioned between said surface of said first filter and said second detector.

13. An apparatus according to claim 11 wherein said second filter has a second radiation wavelength transmission band ($\lambda 2$) deviating from the absorption peak of gas components to be analyzed.

14. An apparatus according to claim 11 wherein said radiation wavelength transmission bands of said first and second filters are in the infrared region of radiation.

15. An apparatus according to claim 11 wherein said apparatus is further defined as one for analyzing an alcohol component that may be present in the respiratory air of a person and wherein said radiation wavelength transmission band ($\lambda 1$) of said first filter is in a range of 10 $\mu m$ and wherein said radiation wavelength transmission band ($\lambda 2$) of said second filter is in a range of 10.6 $\mu m$ and has a bandwidth of ±50 nm at maximum.

16. An apparatus according to claim 11 wherein said arrangement is further defined as one for analyzing an alcohol component that may be present in the respiratory air of a person and wherein said radiation wavelength transmission band ($\lambda 1$) of said first filter is in a range of 3.5 $\mu m$ and wherein said radiation wavelength transmission band of said second filter is in a range of 3.7 $\mu m$ and has a bandwidth of ±50 nm at maximum.

17. A apparatus according to claim 1 wherein said second detector is positioned such that an angle between the path of the radiation beam applied to said surface of said first filter and a path of the reflectived radiation received by said second detector when said first filter is moved to said given one of said plurality of positions of said first filter is within an angular range of 20° to 140°.

18. An apparatus according to claim 17 wherein said angle is within an angular range of 40° to 70°.

19. An apparatus according to claim 1 further comprising moving means for moving said first filter to a plurality of inclined positions, including a position in which specular reflection of radiation to said second detector occurs.

20. An apparatus according to claim 19 wherein said moving means moves said first filter to a predetermined number of inclined positions for altering said wavelength transmission band of said first filter, and wherein said moving means maintains said first filter in each of said inclined positions for a predetermined period of time.

21. An apparatus according to claim 20, wherein said moving means maintains said first filter in an inclined position for a period up to 300 ms.

22. An apparatus according to claim 21 wherein said moving means maintains said first filter in an inclined position for a period between 50 ms and 150 ms.

23. An apparatus according to claim 19 wherein said moving means is further defined as establishing a number of inclined positions as a function of the number of gas components to be analyzed in the gas mixture.

24. An arrangement according to claim 1 further defined as one for analyzing the respiratory air of a person.

25. An apparatus according to claim 1 further including position calculating means (22) coupled to said second detector (2) for determining, from the reflected radiation, the inclined positions of said first filter and the relationship between the inclined positions and the alteration of said radiation wavelength transmission band.

26. An apparatus for analyzing the breathing gases of a person for alcohol, the analysis being carried out on the basis of infra red radiation absorption properties, said apparatus comprising:

a radiation source for providing an infra red radiation beam;

a measuring chamber (6) for selectively receiving the breathing gases of a person or ambient air, said measuring chamber having at least one radiation transmissive window (7a, 7b) for the radiation of said radiation source, radiation from said radiation source passing through the contents of said measuring chamber;

a first detector (1) for receiving radiation that has passed through said measuring chamber;

a first optical interference band pass filter (3) interposed in front of said detector along a path of said radiation beam, said first filter having a surface to which is applied radiation that has passed through said measuring chamber, said first filter having a radiation wavelength transmission band ($\lambda 1$) for transmitting radiation of the transmission band wavelength through the filter to said first detector, said surface reflecting radiation having wavelengths outside said radiation wavelength transmission band, said first filter being movable to a plurality of positions inclined with respect to the radiation beam for altering said radiation wavelength transmission band of said first filter, movement of said first filter causing movement of the radiation reflected from said surface;

a second detector (2) positioned with respect to said first filter for receiving radiation reflected from said surface when said first filter is moved to a given one of said plurality of positions of said first filter;

means coupled to said first detector for analyzing the breathing gases for alcohol on the basis of radiation received by said first detector when said first filter is in a plurality of positions; and comparison means coupled to said first and second detectors for establishing a relationship between the transmitted radiation received by said first detector and the reflected radiation received by said second detector at said given one of said plurality of positions of said first filter when ambient air is in said measuring chamber for determining the suitability of ambient air as a reference gas mixture.

27. A method for analyzing a gas mixture for one or more gas components that may be present in the gas mixture, the analysis of the one or more gas components being carried out on the basis of radiation absorption properties, said method comprising steps of:

providing a sample of a reference gas mixture;

passing a beam of radiation through the sample for absorption by the reference gas mixture;

applying the radiation passed through the reference gas mixture sample to a first optical interference bandpass filter, which has a first radiation wavelength transmission band;

placing the first filter in a given inclined position with respect to the beam of radiation;

allowing a portion of the radiation having wavelengths outside the first radiation wavelength transmission band to reflect from the first filter;

detecting an intensity of the radiation transmitted through the first filter and detecting an intensity of the radiation reflected from the first filter to determine a characteristic of the reference gas mixture;

providing a sample of the gas mixture to be analyzed;

passing the radiation through the gas mixture sample for absorption by the gas mixture to be analyzed;

applying the radiation passed through the gas mixture sample to be analyzed to the first filter;

moving the first filter to a plurality of inclined positions to provide wavelength shifting of the first radiation wavelength transmission band; and detecting the intensity of the radiation passed through said gas mixture sample and transmitted through the first filter at the plurality of the inclined positions to analyze the one or more components of the gas mixture.

28. A method according to claim 27 further comprising a step of applying the reflected radiation to a second optical interference filter having a second radiation wavelength transmission band.

29. A method according to claim 28, the method further comprising the steps of:

selecting the first radiation wavelength transmission band of the first filter so as to include an absorption peak of a gas mixture component which is to be analyzed; and selecting the second radiation wavelength transmission band of the second optical interference filter deviating from the absorption peaks of the gas components to be analyzed.

30. A method according to claim 29 further defined as one for analyzing the gas mixture for alcohol and wherein the first transmission band is selected to be in a range of 10 $\mu$m and the second transmission band is selected to be in a range of 10.6 $\mu$m.

31. A method according to claim 30 further defined as analyzing the respiratory air of a person for alcohol.

32. A method according to claim 29 further defined as one for analyzing a gas mixture for alcohol and wherein the first transmission band is selected to be in a range of 3.5 $\mu$m and the second transmission band is selected to be in a range of 3.7 $\mu$m.

33. A method according to claim 21 further comprising, prior to providing a sample of the reference gas mixture, the steps of:

providing a sample of a calibrating gas mixture;

passing said radiation through the calibrating gas mixture; and detecting an intensity of the radiation transmitted through the first filter and an intensity of the radiation reflected from the first filter at the given inclined position of the first filter.

34. A method according to claim 33 further comprising the step of determining a first relationship between the transmitted radiation intensity and the reflected radiation intensity for the calibrating gas mixture sample.

35. A method according to claim 34 further comprising the steps of:

determining a second relationship between the transmitted radiation intensity and the reflected radiation intensity for the reference gas mixture sample;

comparing the second relationship with the first relationship to determine a characteristic of the reference gas mixture; and controlling the carrying out of the steps of the method in accordance with the comparison of the first relationship and the second relationship.

36. A method according to claim 35 further defined as one for analyzing the respiratory air, of a person for alcohol and as allowing measuring for a concentration of alcohol in the respiratory air of the person if the difference between the first relationship and the second relationship is smaller than a predetermined value.

37. A method for analyzing a gas mixture for one or more gas components that may be present in the gas mixture, said process comprising the steps of:

providing a sample of the gas mixture;

passing a beam of radiation through the sample for absorption by the gas mixture;

applying the radiation passed through the gas mixture sample to a radiation input surface of a first optical interference bandpass filter which has a first radiation wavelength transmission band;

moving the first filter to a plurality of positions that are inclined with respect to the beam of radiation to provide a wavelength shifting of the first radiation wavelength transmission band;

allowing a portion of the radiation having wavelengths outside the first radiation wavelength transmission band to reflect from the radiation input surface;

detecting an inclined position of the first filter for which specular reflection of said radiation to a second detector directed towards the radiation input surface of the first optical interference filter occurs; and calculating, for the inclined position of the first filter, a center wavelength of the first radiation wavelength transmission band.

38. A method according to claim 37, further comprising the step of calculating a connection between predetermined inclined positions, respective center wavelengths and effective wavelength distributions of the first radiation wavelength transmission band.

39. A method according to claim 38, further comprising, prior to providing the sample of said gas mixture, the steps of:

providing a sample of a reference gas mixture;

passing said radiation through the reference gas sample;

detecting an intensity of the radiation transmitted through the first filter and an intensity of the radiation reflected from the first filter at least one of inclined position of the first filter; and determining a first relationship between the transmitted radiation intensity and the reflected radiation intensity indicative of a characteristic of the reference gas mixture.

40. A method according to claim 39, further comprising, prior to providing a sample of said reference gas mixture, the steps of:

providing a sample of a calibrating gas mixture;

passing said radiation through the calibrating gas sample;

detecting an intensity of the radiation transmitted through the first filter and an intensity of the radiation reflected from the first filter at least one inclined position of the first filter; and determining a second relationship between said transmitted radiation intensity and said reflected radiation intensity.

41. A method according to claim 40, further comprising the steps of:

comparing said first relationship and said second relationship; and controlling the carrying out of the steps of the method in accordance with the comparison of the first relationship and the second relationship.

* * * * *